United States Patent
Stormby et al.

(10) Patent No.: US 6,596,001 B2
(45) Date of Patent: Jul. 22, 2003

(54) AIMING DEVICE FOR SURGICAL INSTRUMENT AND METHOD FOR USE FOR TREATING FEMALE URINARY INCONTINENCE

(75) Inventors: Johan Stormby, Malmo (SE); Jorn Lehe, Den Haag (NE); Susanne Landgrebe, Sulfeld (DE); Jochen Hoepffner, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/840,614

(22) Filed: Apr. 23, 2001

(65) Prior Publication Data

US 2002/0068948 A1 Jun. 6, 2002

Related U.S. Application Data

(60) Provisional application No. 60/200,805, filed on May 1, 2000.

(51) Int. Cl.[7] .............................................. A61B 17/12
(52) U.S. Cl. ........................ 606/144; 606/145; 600/29; 600/30
(58) Field of Search ................................ 606/144, 145, 606/223, 224, 225, 102; 600/29, 30, 135, 138, 141, 142

(56) References Cited

U.S. PATENT DOCUMENTS

| 2,213,830 A | * | 9/1940 | Anastasi ....................... 606/145 |
| 2,286,578 A | * | 6/1942 | Sauter .......................... 606/145 |
| 4,373,530 A | * | 2/1983 | Kilejian ........................ 606/145 |
| 5,112,344 A | | 5/1992 | Petros |
| 5,899,909 A | | 5/1999 | Claren et al. |
| 6,273,852 B1 | * | 8/2001 | Lehe et al. .................... 600/30 |

* cited by examiner

*Primary Examiner*—Julian W. Woo

(57) ABSTRACT

Described is a surgical instrument and method for treating female urinary stress incontinence. The instrument includes a curved needle-like element defining in part a curved shaft having a distal end and a proximal end. A tape attaches to the needle for implanting into the lower abdomen of a female to provide support to the urethra. The tape may be made from synthetic and natural materials. The needle and tape may also be modified to allow the surgeon to attach and detach the tape during the surgical operation. The needle attaches to a handle on which attaches a mechanical arm to track the position of the needle point as it passes through the body and exits the abdominal wall.

8 Claims, 17 Drawing Sheets

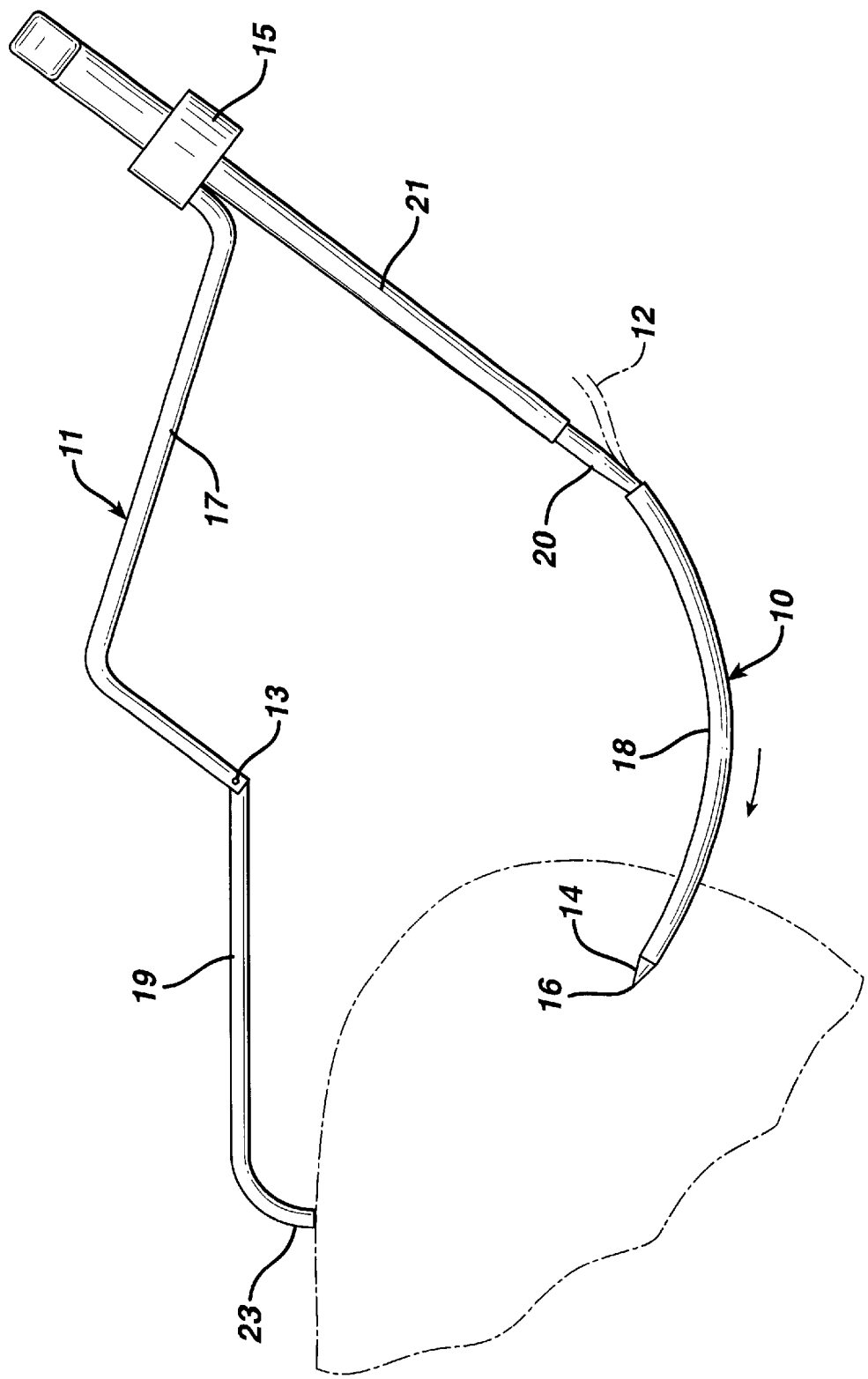

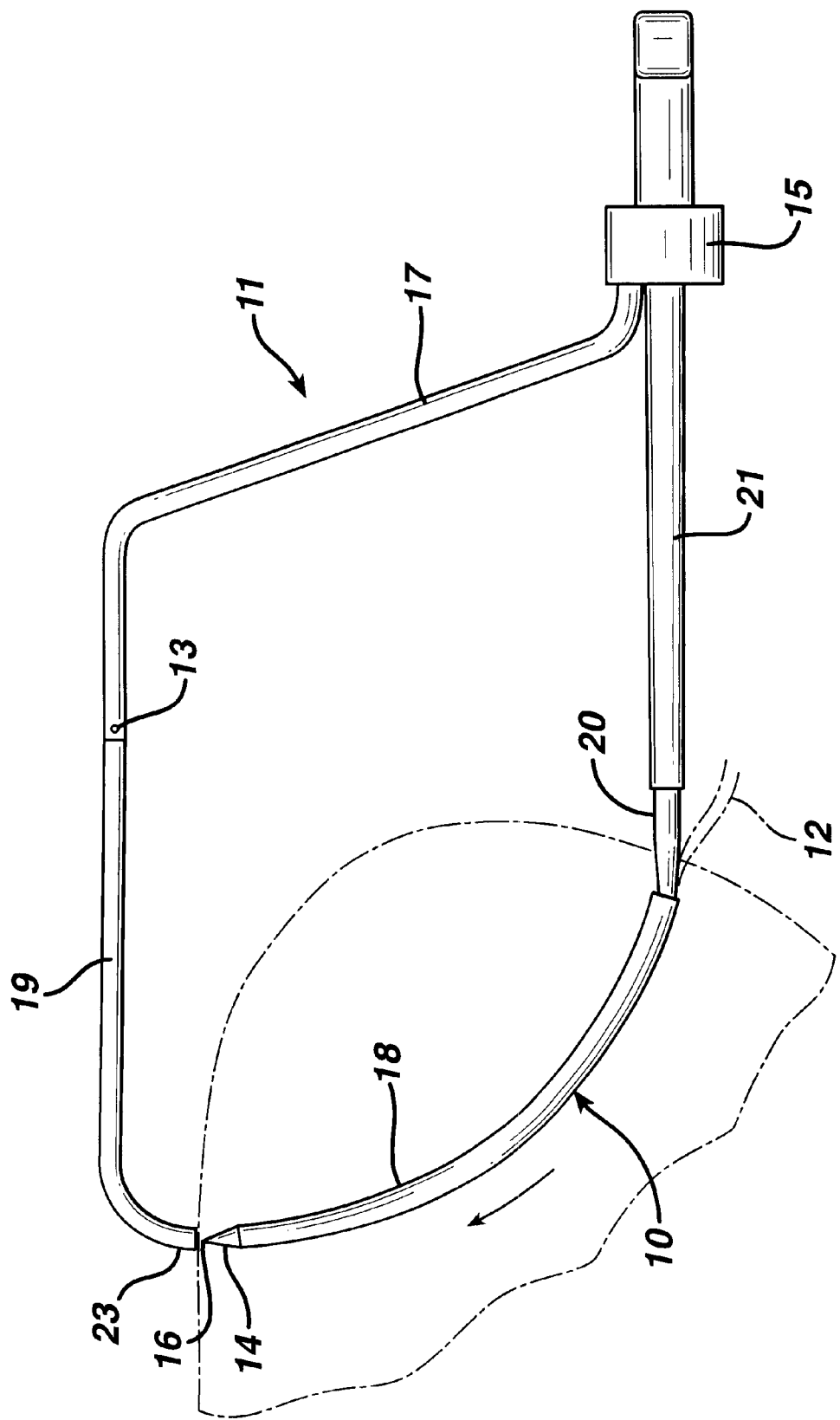

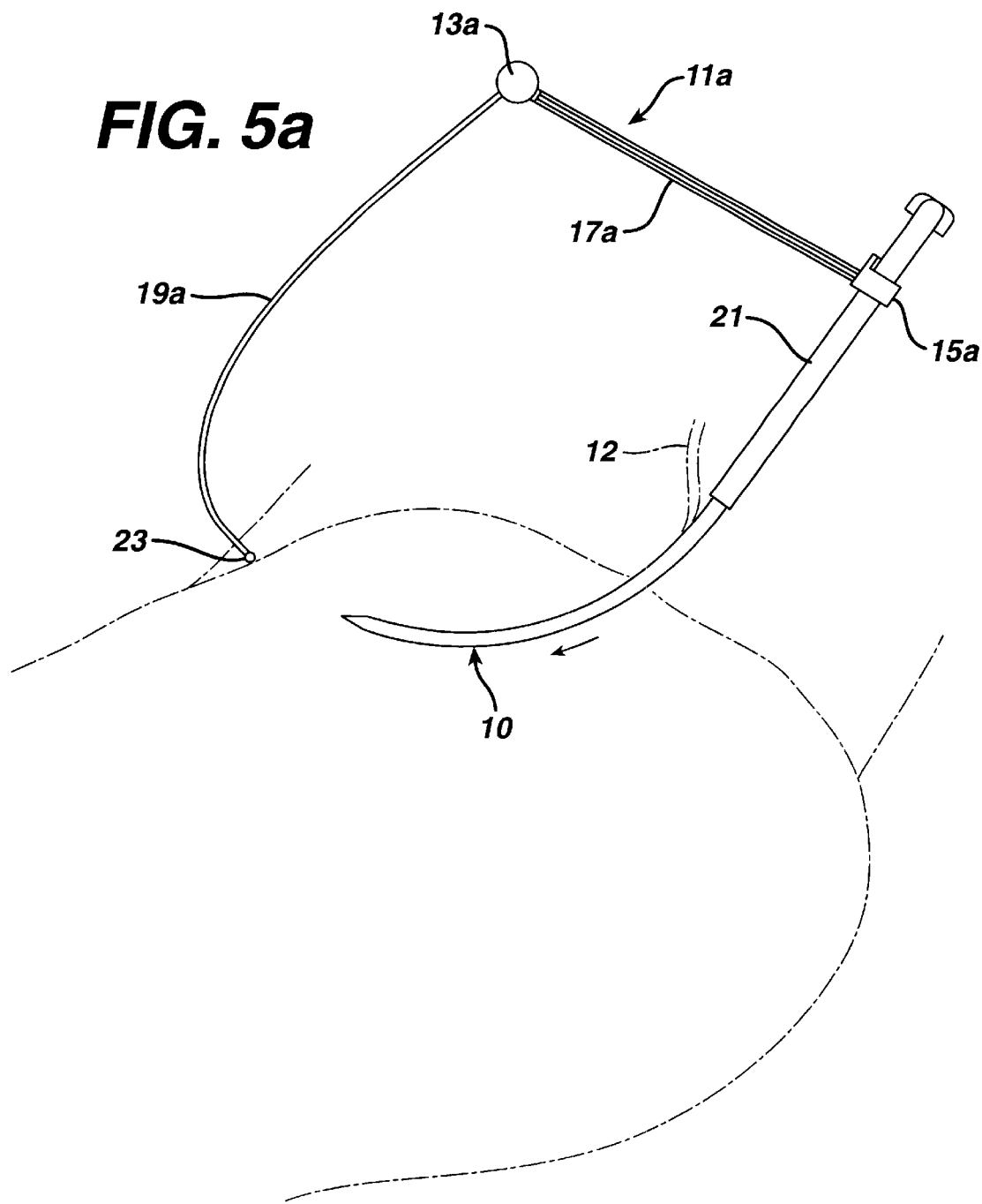

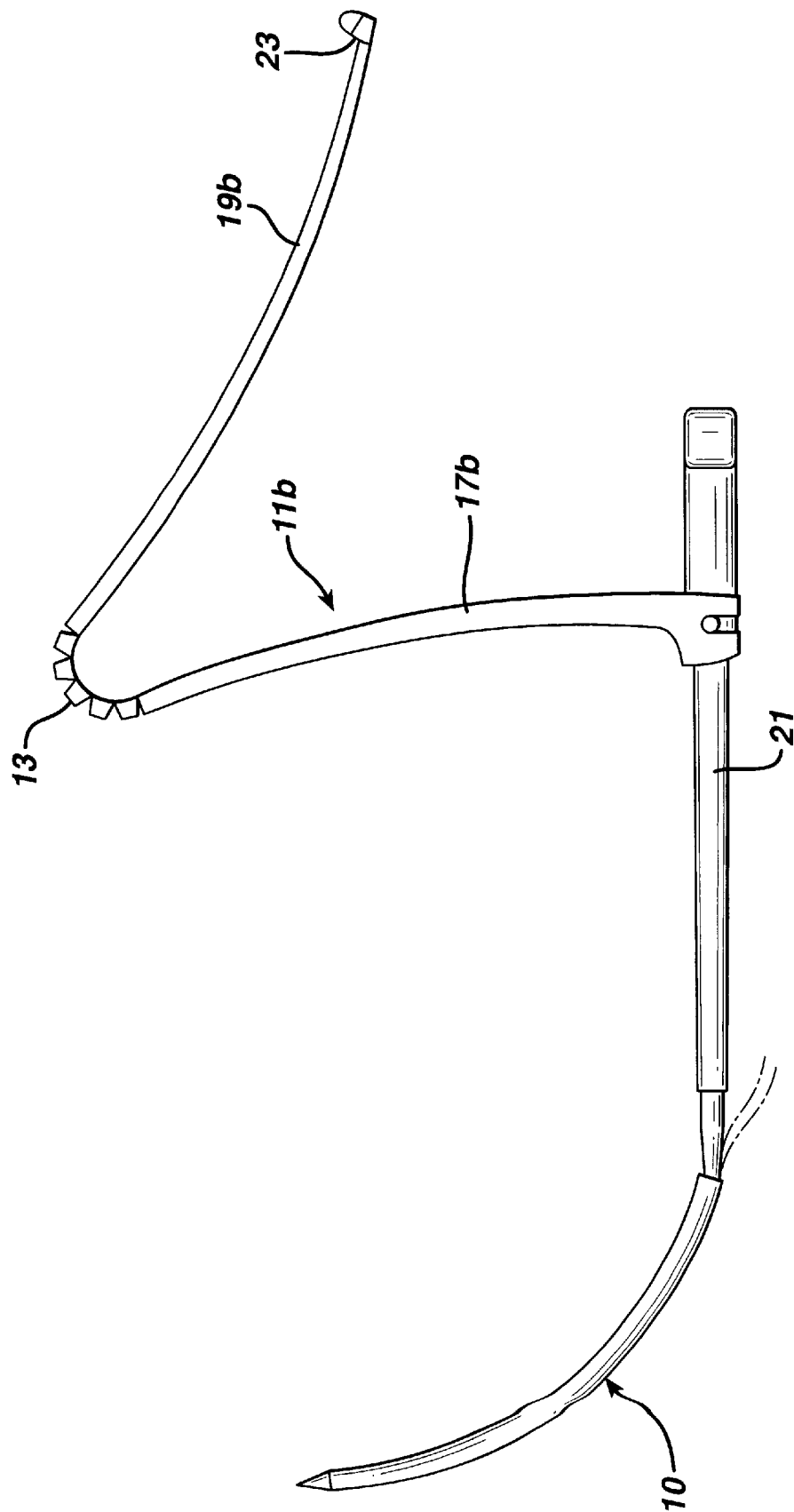

AIMING DEVICE FOR SURGICAL INSTRUMENT AND METHOD FOR USE FOR TREATING FEMALE URINARY INCONTINENCE

CROSS REFERENCE TO RELATED APPLICATION

This application claims the benefit of earlier-filed United States provisional patent application Ser. No. 60/200,805, filed on May 1, 2000, which is incorporated herein by reference in its entirety.

BACKGROUND OF THE INVENTION

The present invention relates generally to a surgical instrument and a method for treating female urinary incontinence and in particular to a needle and an external aiming device to facilitate navigation of the needle through the abdomen cavity.

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, tightening the loop to bring the vaginal wall the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one end of a tape intended to be implanted into the body. In practice, the tape is passed into the body via the vagina first at one end and then at the other end at one side and the other, respectively, of the urethra to form a loop around the urethra, located between the urethra and vaginal wall. The tape is extended over the pubis and through the abdominal wall and is tightened. The tape ends are cut at the abdominal wall, and the tape is left implanted in the body. U.S. Pat. No. 5,899,909 is incorporated herein by reference.

Current methods for treating SUI using needles to implant a tape do not provide visual feedback to the surgeon of the location that the needle will penetrate the abdominal wall.

It would be beneficial to provide a simplified means of providing visual feedback to the surgeon as to the needle tip orientation and the location the needle will penetrate the abdominal wall.

The invention is further related to U.S. patent application Ser. Nos. 09/521,801, 09/573,645 and 09/631,559, all assigned to the assignee of the present invention and all incorporated herein by reference.

SUMMARY OF THE INVENTION

The invention overcomes the deficiencies of the prior art and provides for an improved needle for use with an apparatus and a method for the treatment of female stress urinary incontinence. The invention provides a surgical instrument comprising a handle at one end and connecting means at the other end to receive, one at a time, two curved needle-like elements, each of which have a blunt tip and varying diameter. Each needle connects at one end to separate ends of a tape intended to be implanted within the body. In practice, a first end of the tape is passed, via one of the curved needles, into the body via the vagina at one side of the urethra. The needle and first end of the tape pass over the pubis and through the abdominal wall. The second needle element connects to the handle and to the second end of the tape. The needle and second end of the tape pass into the body via the vagina at the opposite site of the urethra from the first end of the tape thereby forming a loop or sling around the urethra with the tape. The second end of the tape is extended over the pubis and through the abdominal wall. The tape ends are cut at the abdominal wall, and the tape is left in the body.

The invention further provides for a single curved needle element having a blunt tip and varying diameter and further provides for an easy attachment means enabling the surgeon to connect both the first and second tape ends to the single needle to perform the above-stated procedure.

The invention still further provides for a tape comprising of a synthetic mesh in combination with a natural material whereby the natural material would reside below the urethra to eliminate potential erosion issues.

The invention further provides for a mechanical arm attached to the handle that remains exterior to the body. The mechanical arm is designed to track the tip of the needle while the needle penetrates the interior of the abdominal cavity. The resting point of the distal end of the mechanical arm on the abdomen indicates the exit point of the needle.

The object of the invention is to provide a surgical instrument that provides visual feedback to the surgeon as to the approximate locate of the needle tip and the exit point of the needle through the wall of the abdomen.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3–4 are schematic representations of the external navigator in operation while the needle penetrates the body;

FIGS. 5a–b illustrate alternate embodiments of the external navigator;

DETAILED DESCRIPTION OF THE INVENTION

Figure 1:
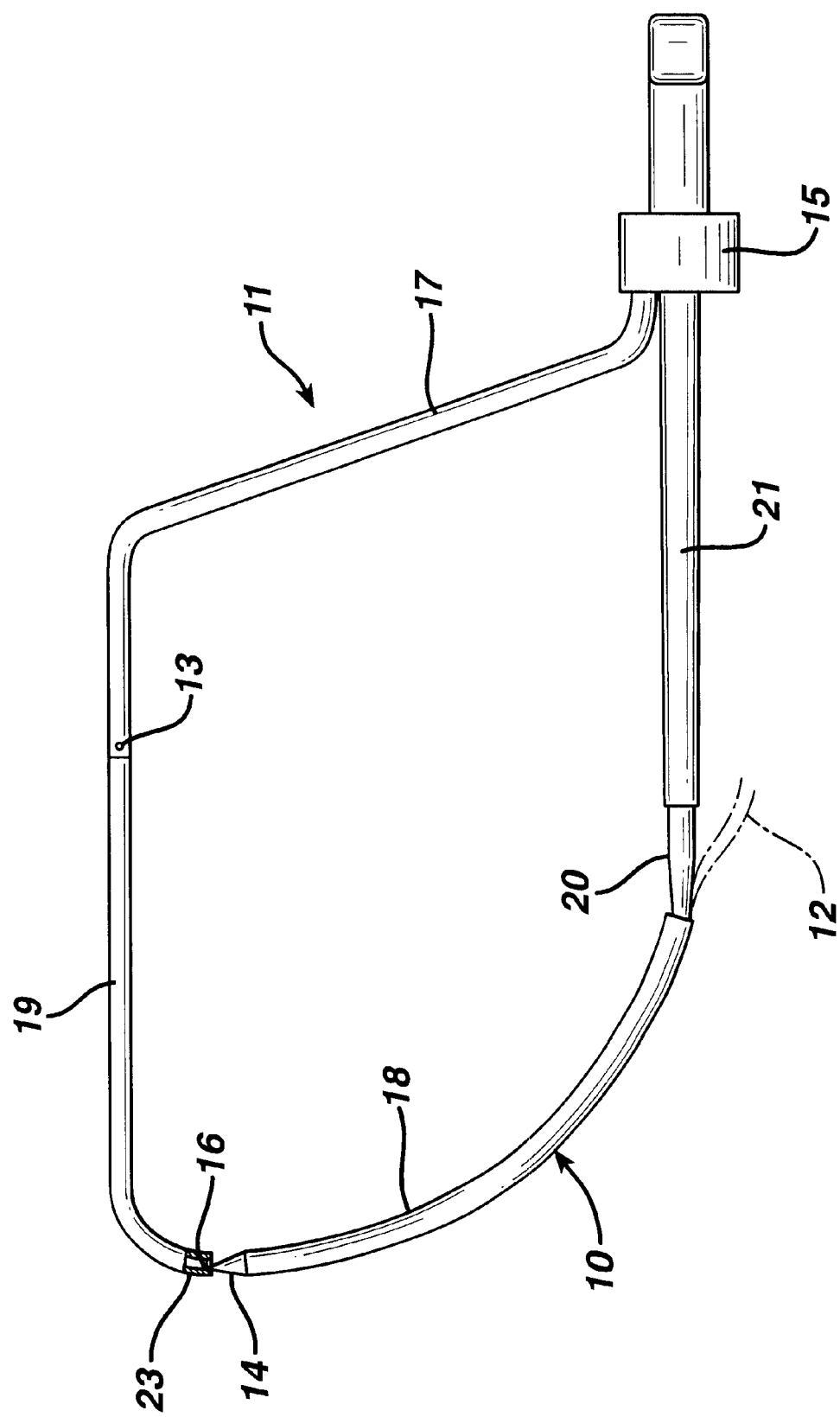
FIG. 1 is a side view of the needle and external navigator in one embodiment thereof.

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the The invention discloses an apparatus and method for treating SUI. A tape is passed through pelvic tissue and positioned underneath the urethra, preferably at the midline of the urethra, creating a supportive sling. The tape provides a structure means for tissue ingrowth and thereby provides a newly created body tissue supporting means for the urethra. When pressure is exerted upon the lower abdomen, such as during a cough or sneeze, the tape provides support to the urethra, allowing it to keep its seal and prevent the unwanted discharge of urine.

Referring to FIGS. 1 through 6, the surgical instrument comprises a needle-like element 10 that attaches to a mesh tape 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the tape as described below.

The proximal end of needle 10 terminates in an attachment segment 20 that is adapted to mate and lock into a handle 21 as disclosed in U.S. Pat. No. 5,899,909, previously incorporated herein by reference.

Disposed between tip 14 and segment 20 is a curved shaft segment 18. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters.

Needle 10 is preferably tubular with a circular cross section and is made from a material that is compatible with the human body. It is also preferred that needle 10 is made from a material that can be autoclaved to enable multiple surgical procedures of needle 10. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the tape 12.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Attached to handle 21 is an aiming device or external navigator 11. Navigator 11 is an approximately Z-shaped mechanical arm that is cantilevered off the proximal end of handle 21 by means of a coupling connector 15 that is preferably attached to handle 21 by means of a set screw or thumb screw. Navigator 11 comprises a stationary arm 17 and an articulating or rotating arm 19. Stationary arm 17 is connected to rotating arm 19 by means of a hinge element 13 as exemplary shown in FIGS. 2a–c. Navigator 11 may be made from a material that can be autoclaved to enable multiple surgical procedures, preferably, AISI 303 stainless. Alternatively, navigator 11 may be made from a plastic, thereby allowing navigator 11 to be a one-time use instrument.

Figure 2:
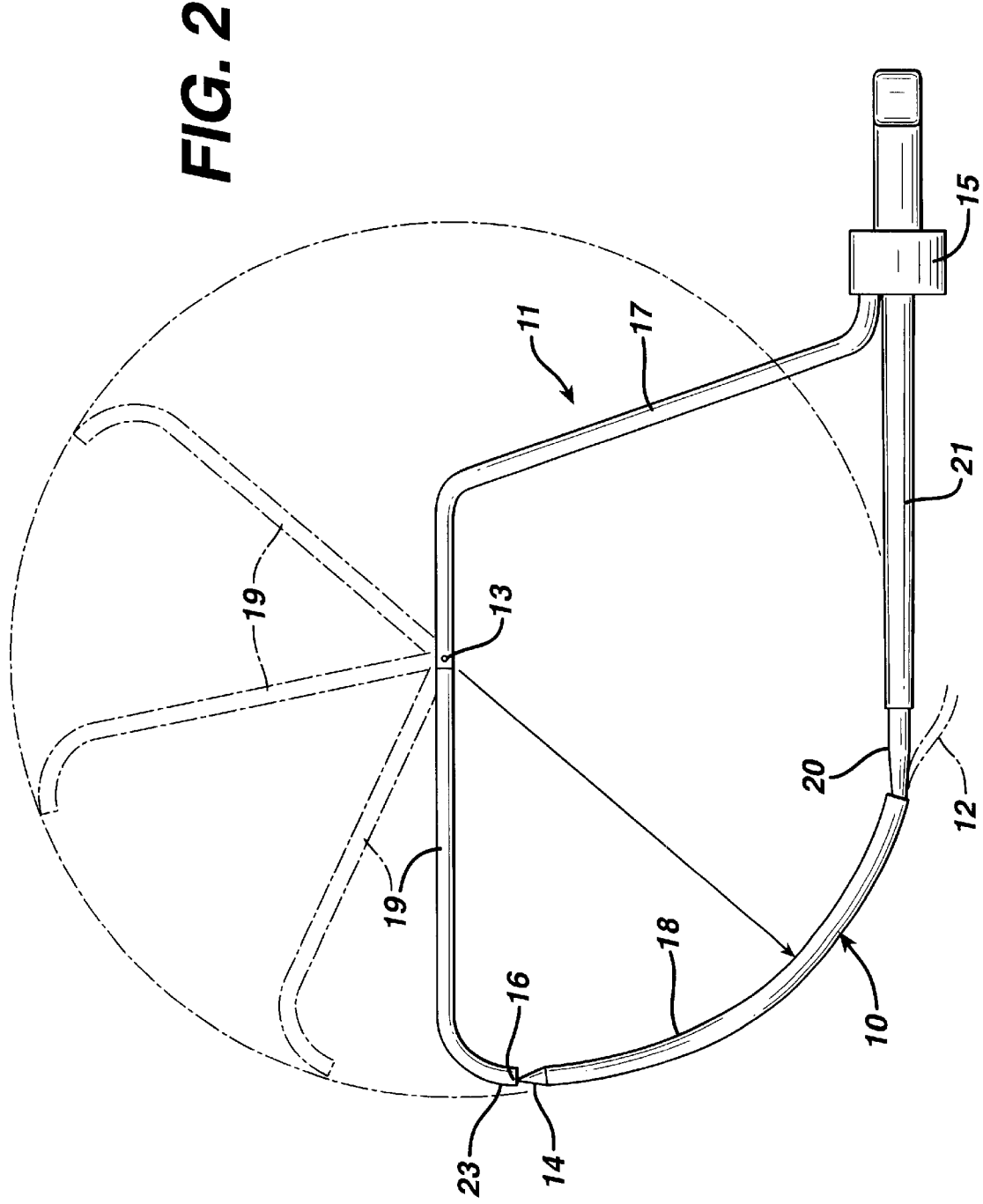
FIG. 2 illustrates the action of the hinged portion of the external navigator.
Figure 2A:
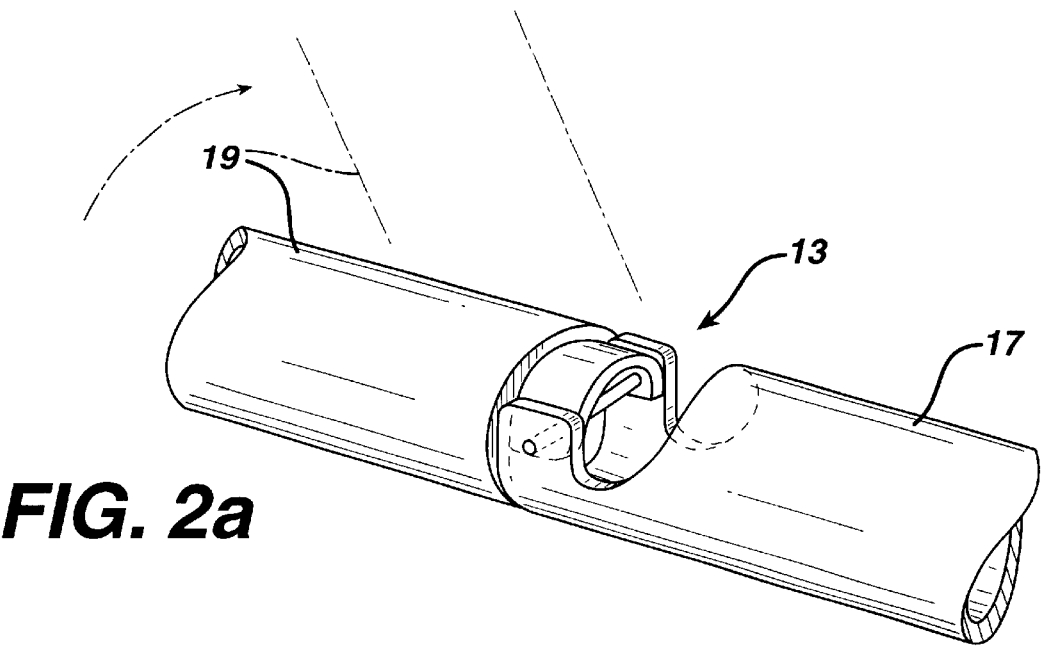
FIGS. 2a–c illustrate alternate hinge mechanisms of the external navigator.
Figure 2B:
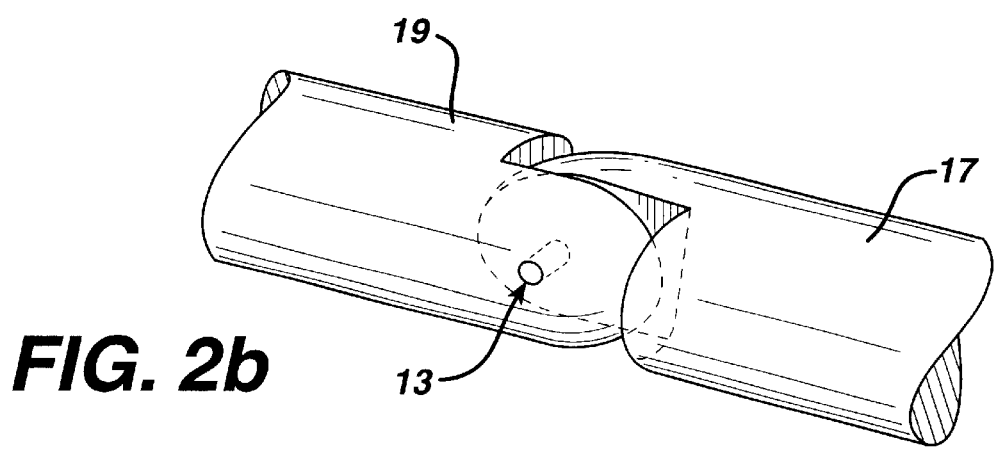
Figure 2C:
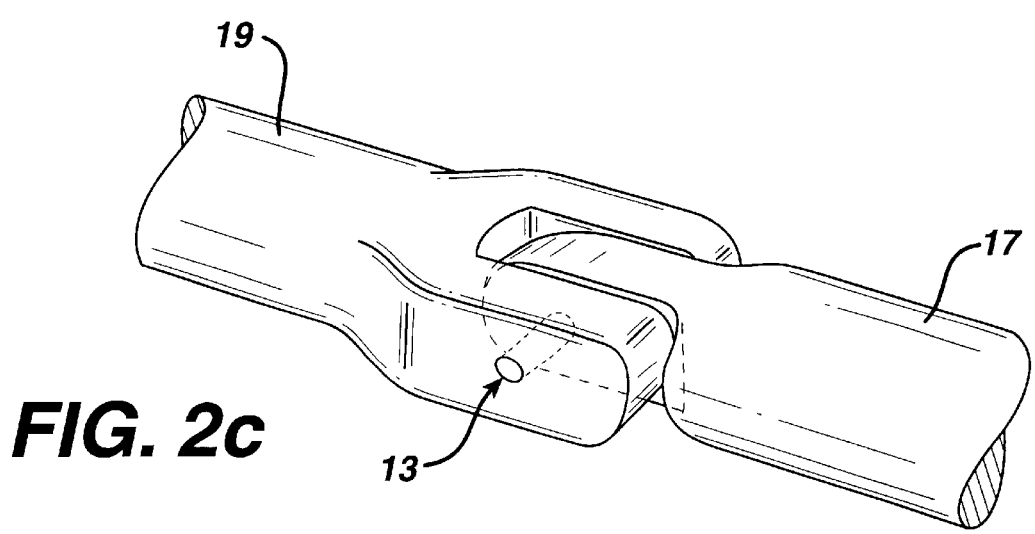

Referring to FIGS. 2–4, the principle of the navigator is shown. In the resting or closed state, tip 16 aligns or coincides with the most distal end 23 of navigator 11. Preferably, distal end 23 is concave in shape to accept tip 16. As needle 10 penetrates the body (shown schematically in FIGS. 3–4), navigator 11 is placed on the external surface of the body in the open position. As needle 10 continues through the body, distal end 23 slides across the body surface and tracks the location of needle tip 16. If the needle tip 16 deviates left or right from its intended trajectory, distal end 23 will also deviate left or right, respectively, thereby alerting the surgeon the needle tip may be off line from the intended placement. Finally, as needle tip 16 emerges from the body, tip 16 and distal end 23 will couple.

As is known to those skilled in the art, navigator 11 may utilize alternate means for aligning its distal end 23 to track needle tip 16. For example, a light source may be utilized within navigator 11 to direct a point of light onto the abdomen to track the position of the needle tip 16. Therefore, alignment or coupling of the distal end 23 with needle tip 16 is not limited to physical alignment or coupling, but rather any means, such as a light source, that allows the navigator distal end 23 to track the location of needle tip 16.

FIGS. 5a–b illustrate alternate embodiments of the invention. In FIG. 5a, navigator 11a comprises a straight stationary arm 17a and a rotating arm 19a having a straight portion and a curved distal end. Distal end 23 is represented by a spherical element. Stationary arm 17a is connected to rotating arm by means of a sliding hinge 13a. FIG. 5b illustrates a disposable navigator 11a, made from an appropriate material, such as plastic. In this embodiment, navigator 11b is a single piece. Stationary arm 17b is contiguous with rotating arm 19b by means of hinge element 13b represented as scored material to provided flexibility. The principle of operation for the embodiments 5a–b is the same as that described for FIGS. 2–4.

Figure 6:
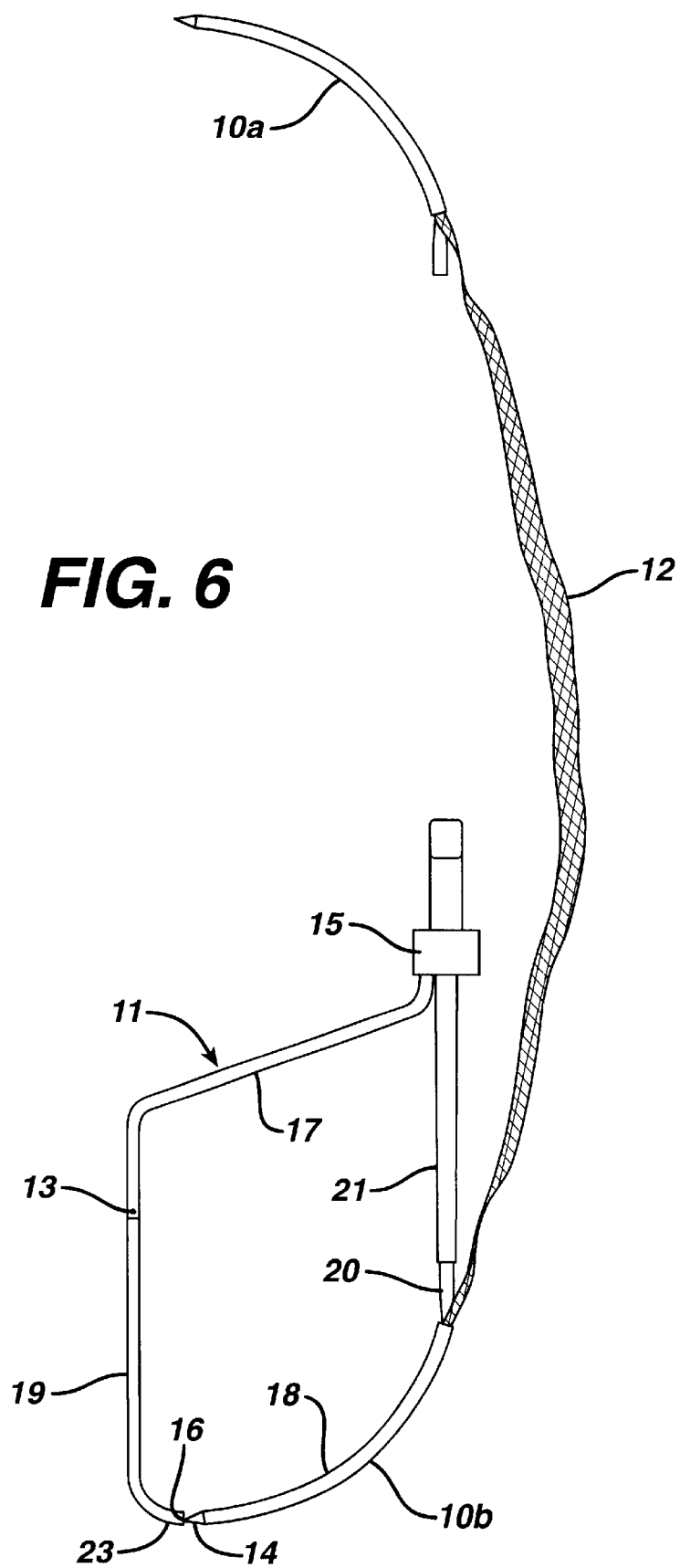
FIG. 6 illustrates an exemplary application of the invention to treat SUI.

The usefulness of the invention will now be described in a surgical procedure to treat female SUI. Referring to FIG. 6, the combined handle 21, needle 10 and navigator 11 is attached to a tape or mesh 12. Tape 12 comprises any tissue-compatible synthetic material, or any natural material, including, but not limited to, autologous, allograft, xenograft, a tissue-engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body.

Tape 12 may be of any convenient shape that suits the intended purpose of the invention. An exemplary width is about 1 cm and the length would be dependent upon the size of the female undergoing the procedure. Tape 12 may be single or double ply, generally planar in structure, or tubular to provide additional supporting strength and more surface area on which tissue fibers may attach. Moreover, tape 12 may consist of different types of material, such as a bioabsorbable and non-bioabsorbable material. Tape 12 may also be coated with an antimicrobial additive to prevent or minimize infection and a lubricous coating, for example, a bioabsorbable hydrogel, to facilitate the tape passing through the tissue as discussed below. Preferably, tape 12 is covered by a removal plastic sheath as disclosed in U.S. Pat. No. 5,899,909. The tape may also be made radio-opaque and/or of a contrasting color to the body tissue to allow for future diagnostic visualization.

In one embodiment tape 12 may be attached to needle segment 20 by means of tying, gluing or other suitable attaching means. Preferably, a biocompatible heat shrink tube fixes tape 12 onto needle portion 20. As would be appreciated by one skilled in the art, there exist multiple means for detachably connecting the tape to the needle.

The surgical procedure for implanting tape 12 using two needles is shown in FIGS. 7a–i. In the figures the relevant parts of the female lower abdomen are disclosed, the vagina being 50, the uterus 52, the urethra 54, the pubic bone 56, the urinary bladder 58 and the abdominal wall 60. The first needle 10a attaches to the handle 21 and penetrates the vaginal wall, an incision having first been made in the wall to create a tissue flap and the distal end 23 of the navigator 11 rests on the abdominal wall 60, FIG. 7a. The surgeon guides needle 10a through the vaginal wall and through the soft tissue on one side of the urethra 54, the needle then according to FIGS. 7b–c being passed close to the back of the pubic bone 56, through additional layers of fat, muscle and fascia, and then through the abdominal wall 60 above the pubic bone 56 and connecting with the distal end 23, the navigator 11 and needle 10 now in the closed position. An incision can be made through the abdominal wall for the passage of the needle therethrough. Handle 21, along with navigator 11, are disconnected from needle 10a, and the needle 10a along with tape 12 are withdrawn from the abdomen wall by means of forceps, FIG. 7d.

Figure 7A:
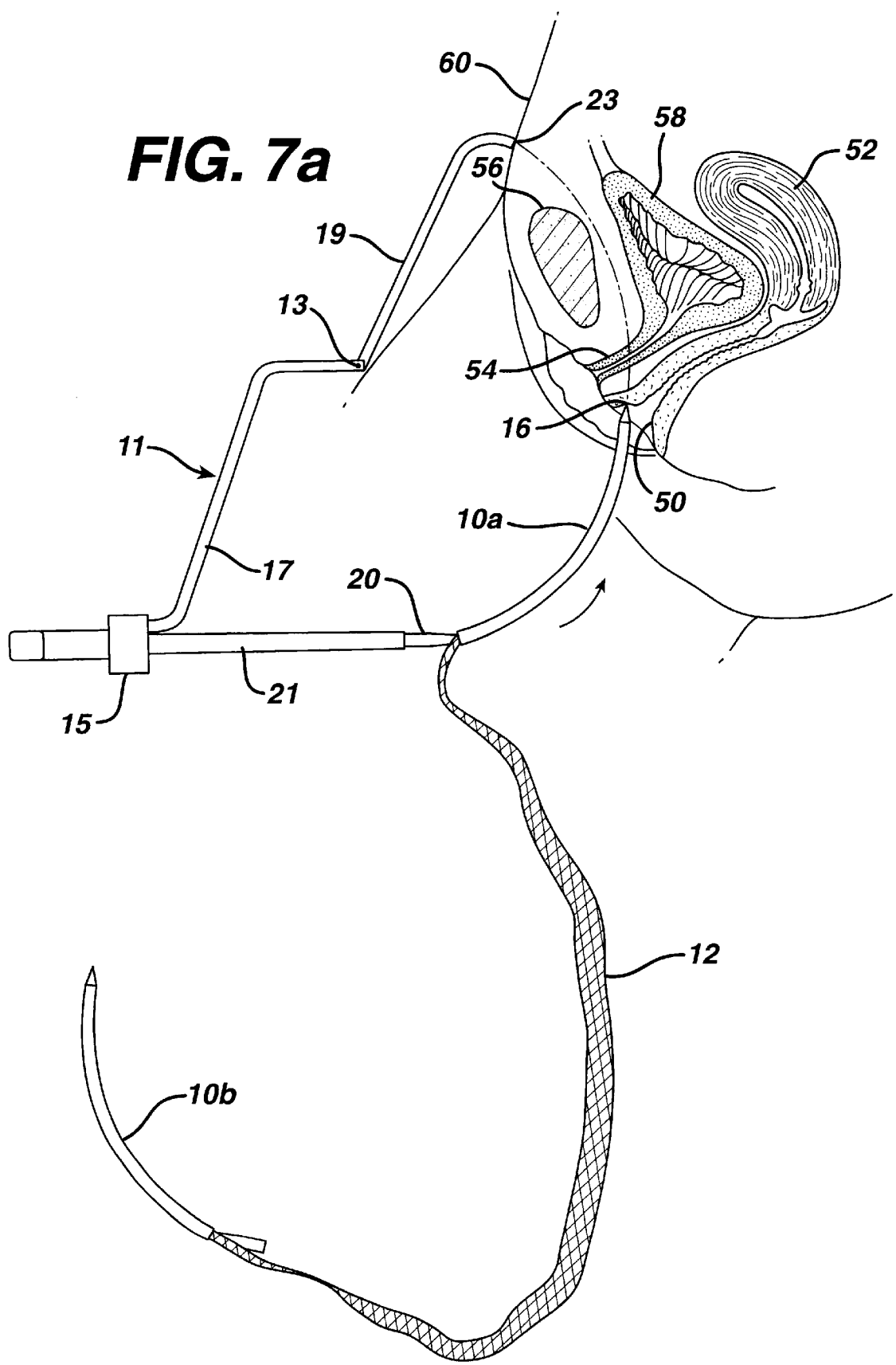
FIGS. 7a–i illustrate the method of passing the mesh tape through the abdomen to treat SUI using the invention.
Figure 7B:
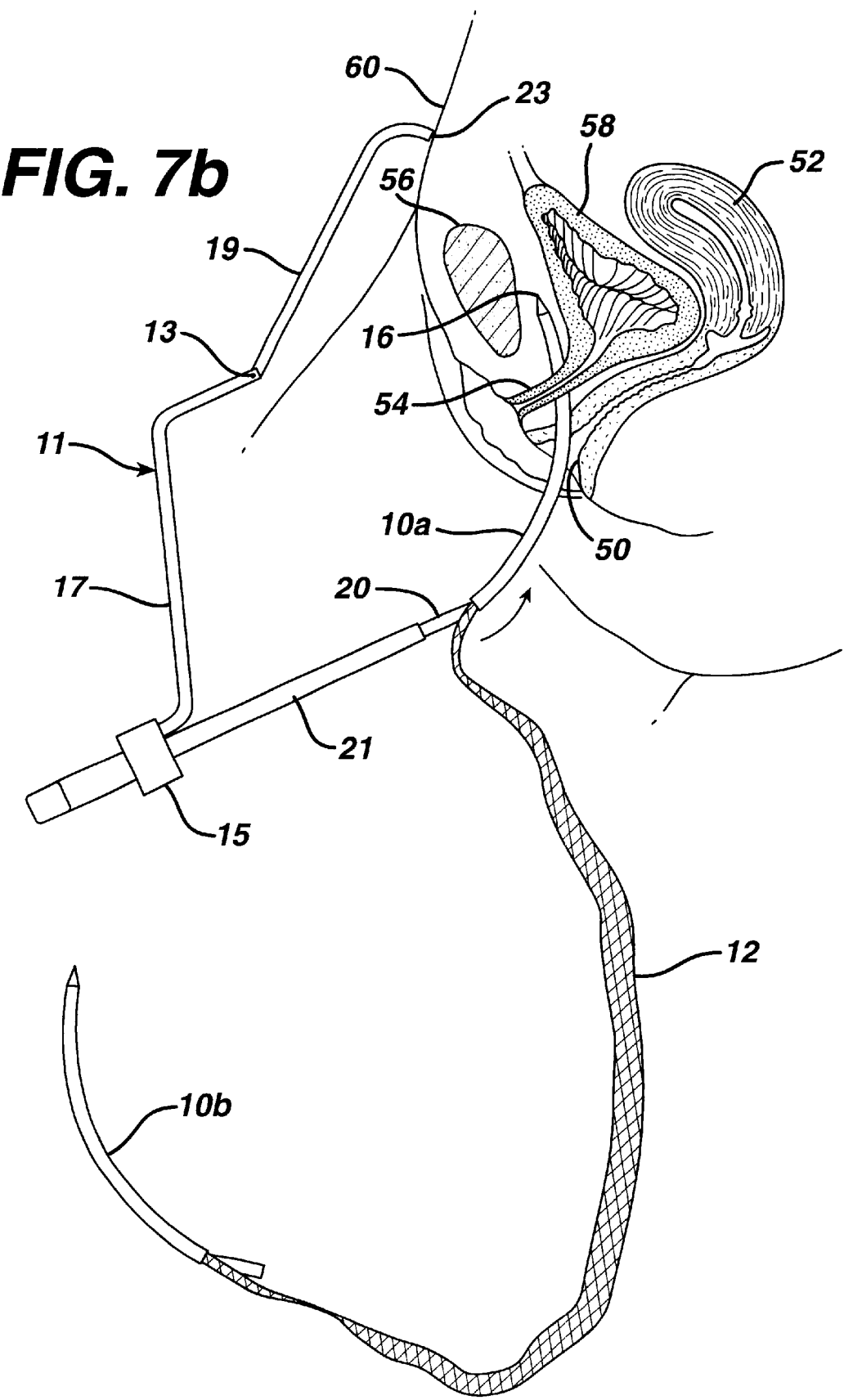
Figure 7C:
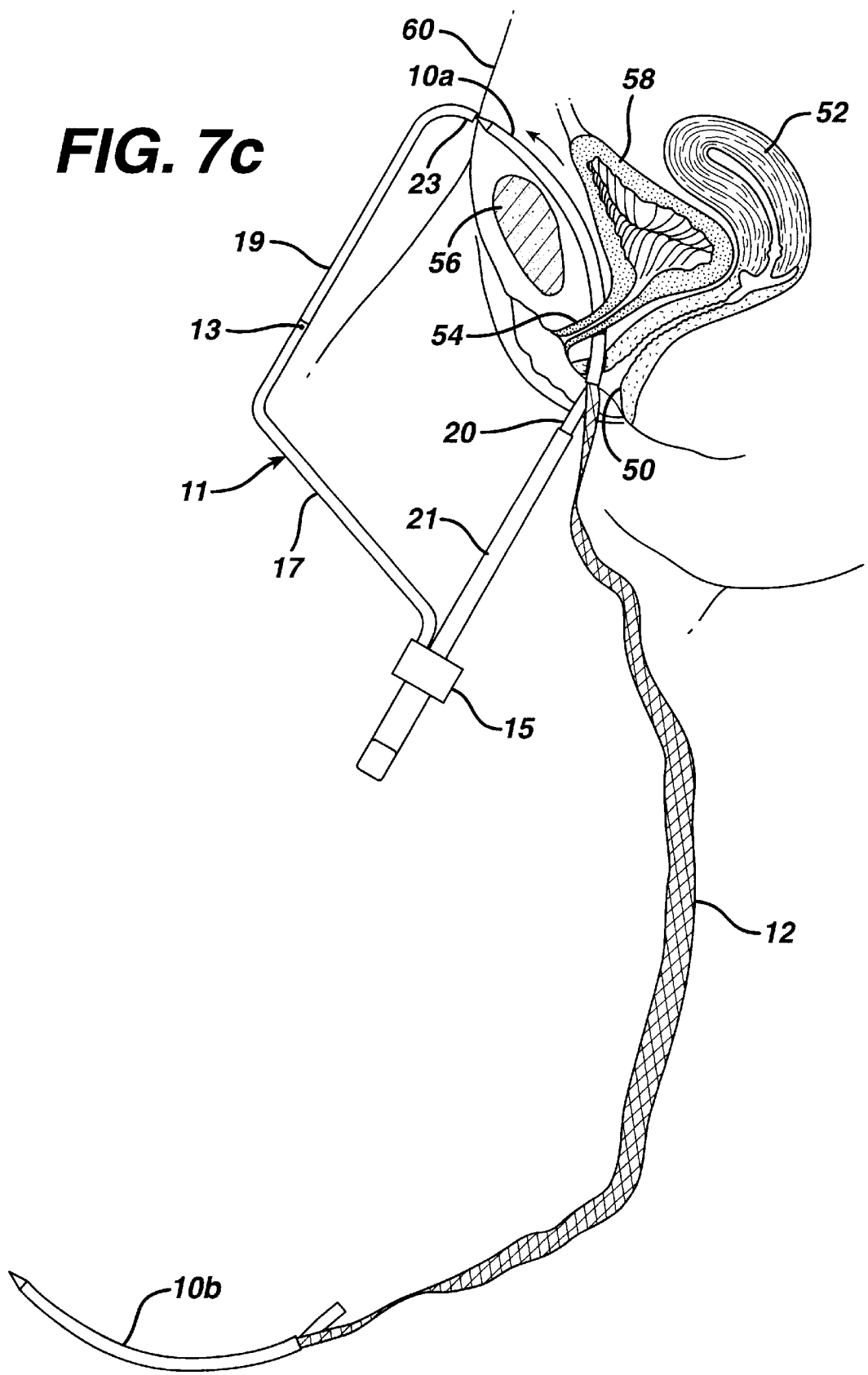
Figure 7D:
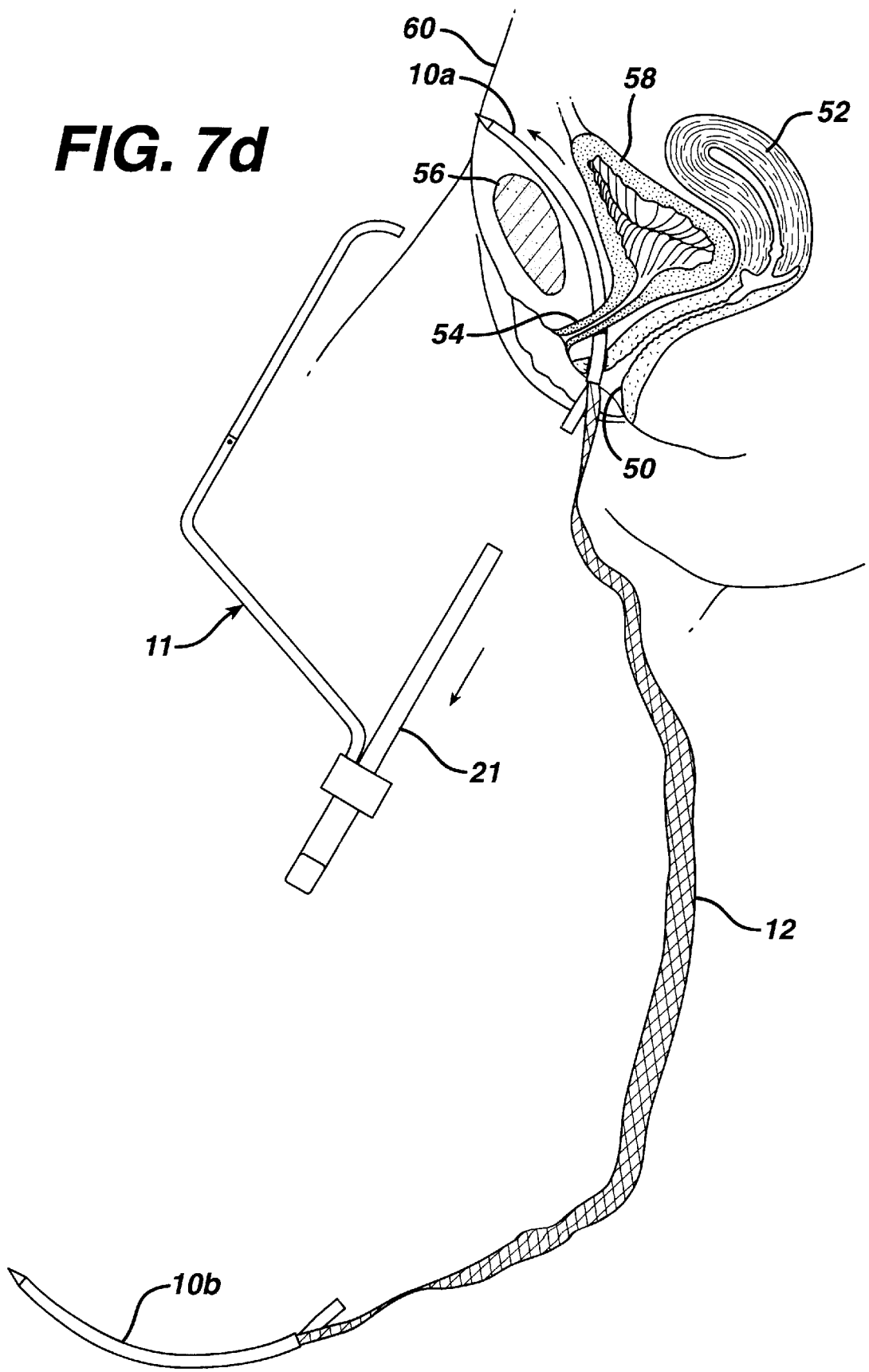
Figure 7E:
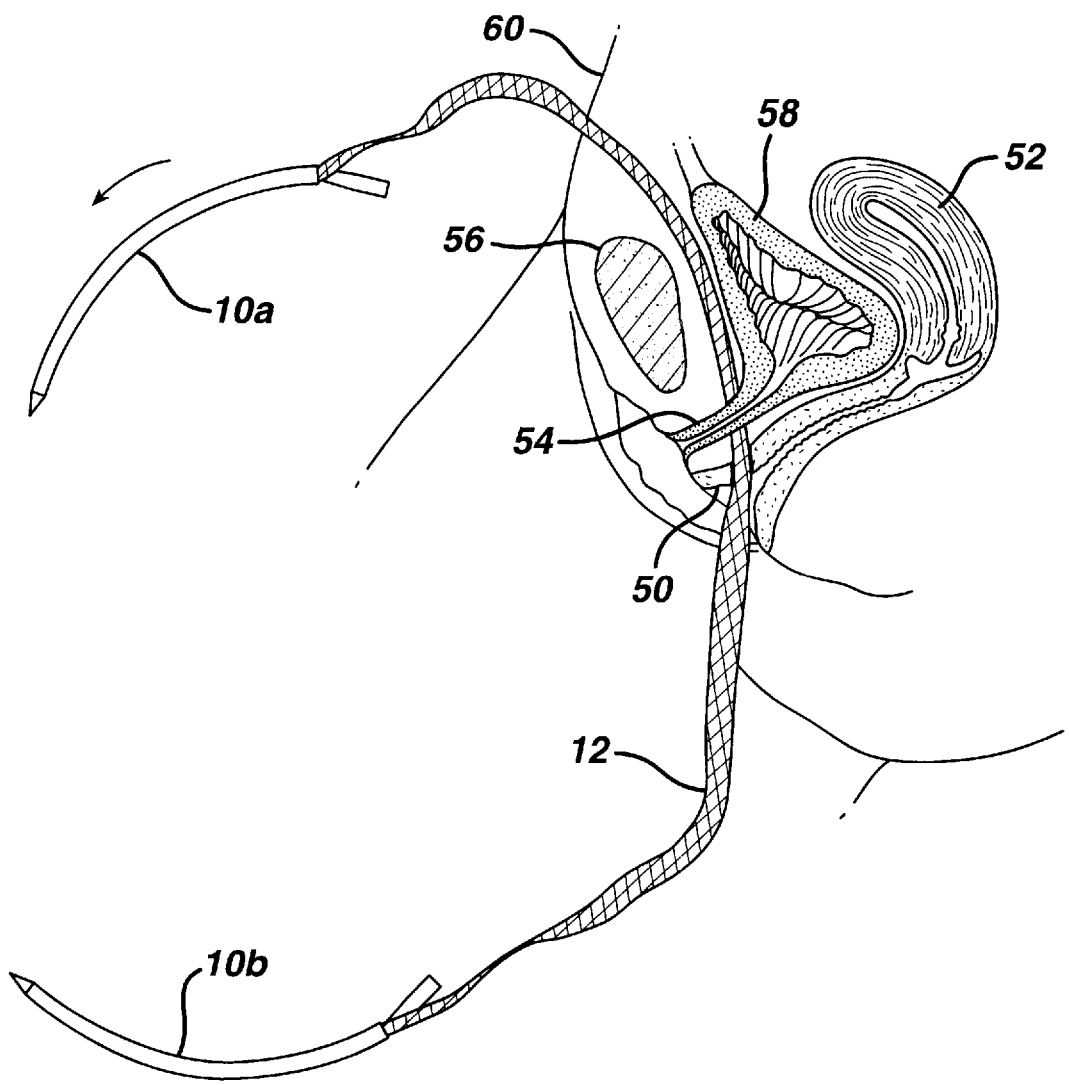
Figure 7F:
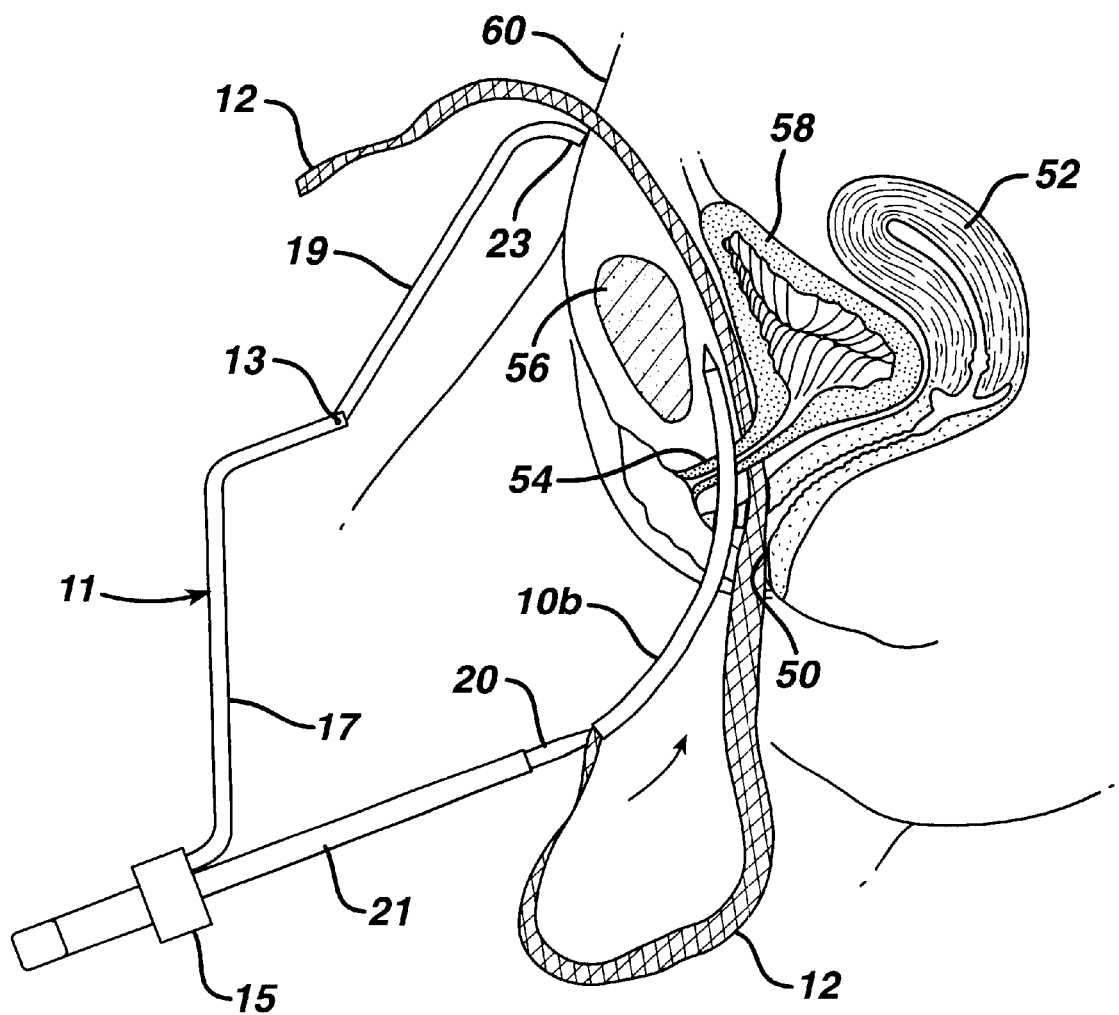
Figure 7G:
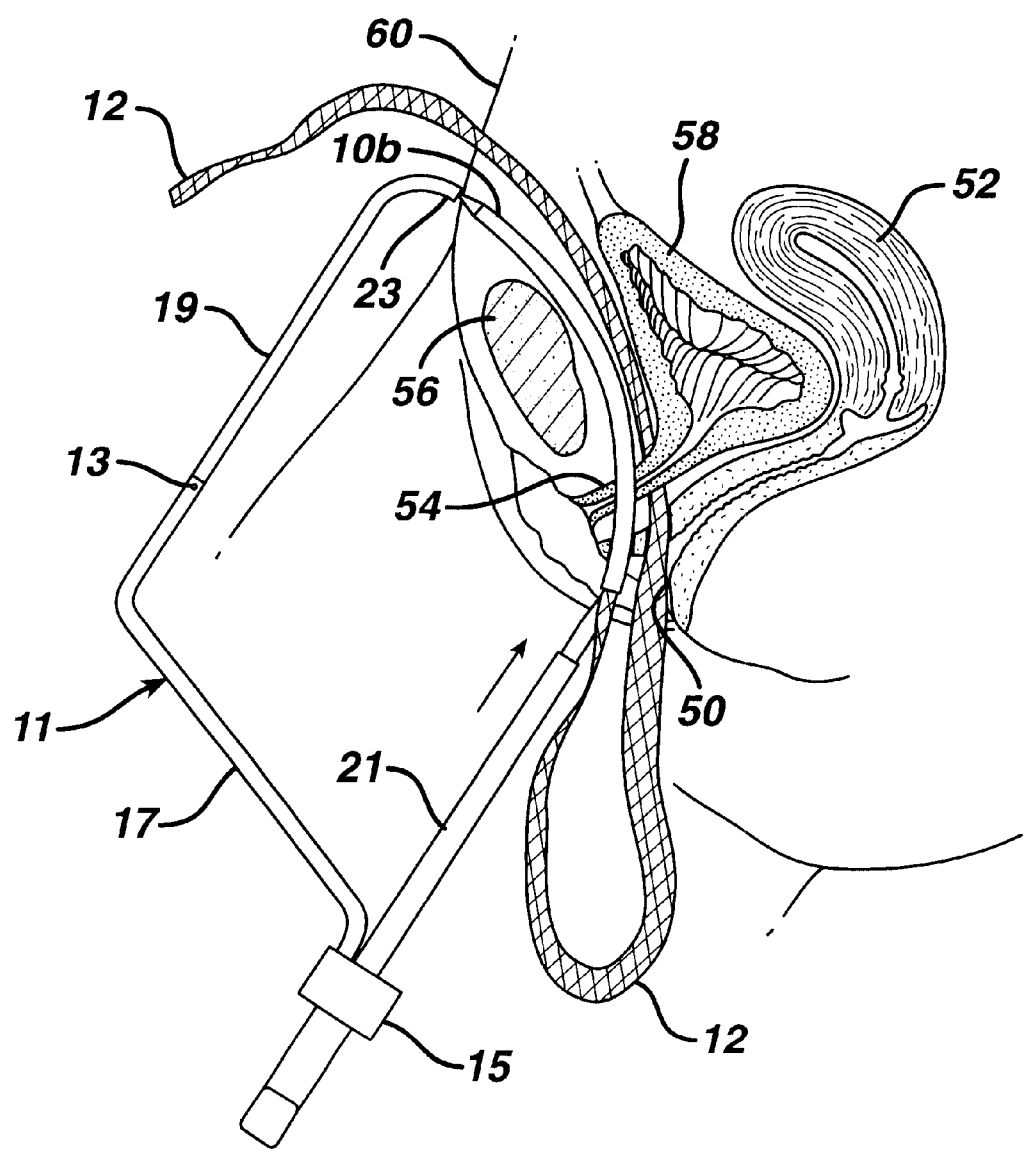
Figure 7H:
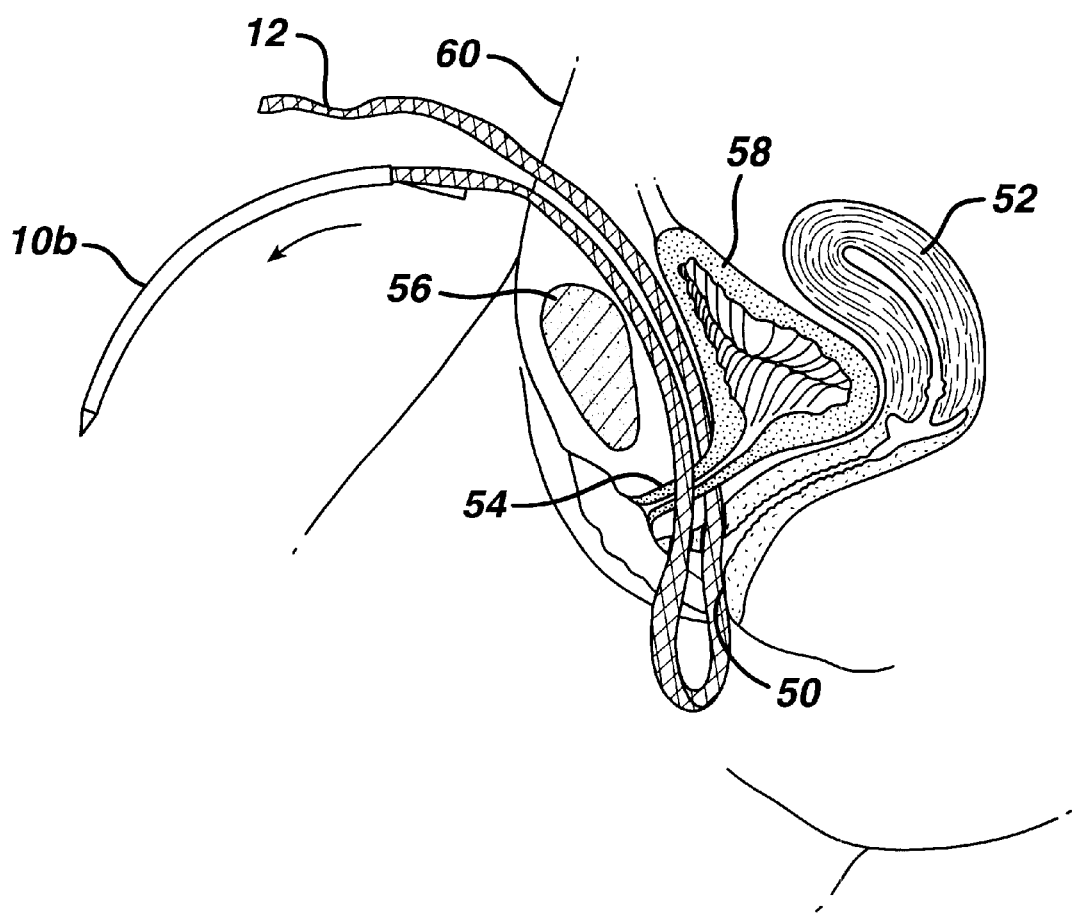
Figure 7I:
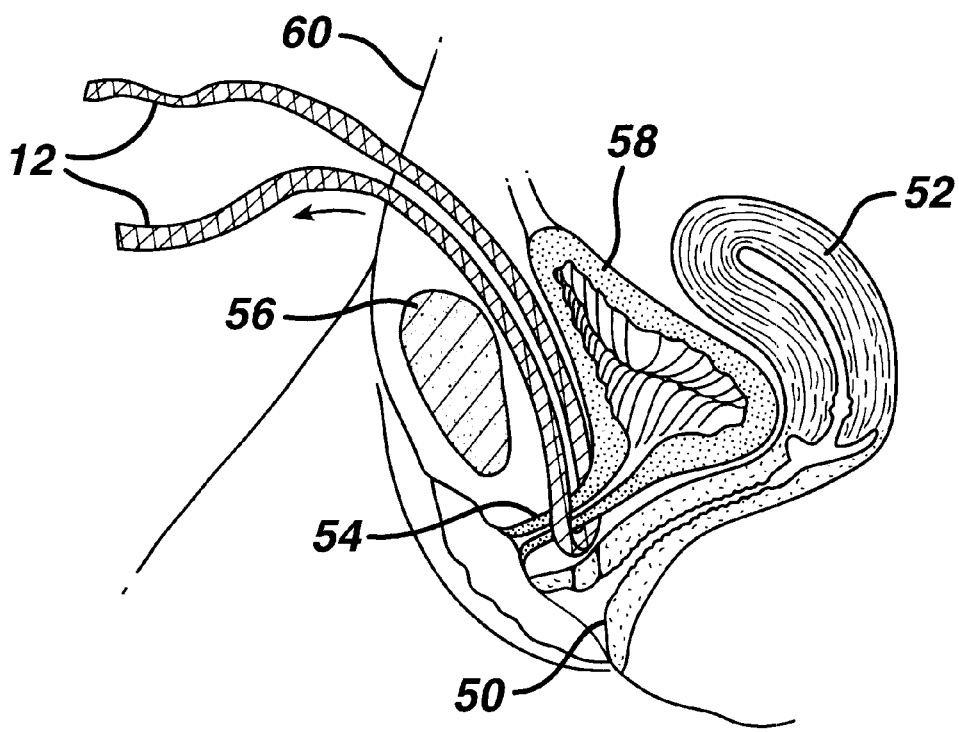

Referring to FIGS. 7e–f, needle 10b is now attached to handle 21 with navigator 11, and needle 10b is passed through the incision in the vaginal wall as guided by the surgeon and through the soft tissue on the opposite side of the urethra than the previous end of tape 12, all along distal end 23 tracking the spatial location of needle tip 16 within the abdomen. Needle 10b passes close to the back of the pubic bone, through additional layers of fat, muscle and fascia, and then through the abdominal wall above the pubic bone and withdrawn, FIGS. 7g–h.

Surgical treatment of SUI may be accomplished is various methods, including a trans-abdominal approach. Accordingly, it is contemplated that this invention is also useful in the various alternative treatment methods.

It is further contemplated that the invention may be used in any number of surgical applications where an instrument is inserted into the body and external navigation of the instrument is contemplated.

Accordingly, it will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A surgical instrument for implanting a device within a patients body to treat female urinary stress incontinence comprising:
   a) a handle;
   b) a surgical element dimensioned for introducing the device into the body, the surgical element defining in part a curved shaft and having a distal end and a proximal end, the proximal end being coupled to the handle so as to fix the surgical element in position relative to the handle; and
   c) an articulating mechanical arm having a distal end and a proximal end, the articulating mechanical arm being coupled to the handle and movable relative to both the handle and surgical element to at least a position in which the distal end of the arm aligns in a predetermined manner with the distal end of the surgical element, the arm further being movable relative to the surgical element and handle and being dimensioned to enable it to remain outside of the body to provide a visual indicator as to the position of the surgical element when it is used to introduce the support device into the body.

2. The surgical instrument of claim 1, wherein the device is a tape that provides support to the urethra.

3. The surgical instrument of claim 1, wherein the mechanical arm comprises a stationary element and a rotating element pivotably coupled to the stationary element so that a distal end of the rotating element travels along an arc that intersects with the distal end of the surgical element.

4. The surgical instrument of claim 3, wherein the stationary element is substantially Z-shaped.

5. A method for treating female urinary incontinence comprising the steps of:
   a) providing a surgical element defining in part a curved shaft and having a distal end and a proximal end and a tape attached thereto;
   b) coupling the proximal end of the surgical instrument to a handle;
   c) providing an articulating mechanical arm connected to the handle and movable relative to the handle to at least a position in which the distal end of the arm aligns in a predetermined manner with the distal end of the surgical element; and
   d) passing the surgical element and tape into the body to form a sling around the urethra while the articulating mechanical arm remains outside of the body to provide a visual indicator as to the position of the surgical element as it is passed through the body.

6. A method for implanting a device within a patients body to treat female urinary incontinence comprising the steps of:
   a) providing a curved element dimensioned for introducing the device into the body, the curved element defining in part a curved shaft and having a proximal and distal end;

b) coupling the proximal end of the curved element to a handle;

b) providing an articulating mechanical arm connected to the handle, and positioned relative to the handle to track the location of the distal end of the curved element from an exterior of the body;

c) attaching a tape to the curved element; and d) passing the curved element and tape into the body to form a sling around the urethra while the articulating mechanical arm remains outside the body to provide a visual indicator of the position of the curved element within the body.

7. A surgical kit for implanting a device in a patient's body to treat female urinary stress incontinence comprising:

a) a surgical element defining in part a curved shaft and having a distal end and a proximal end, the proximal end for connection to a handle; and b) an articulating mechanical arm having a distal end and a proximal end, wherein the proximal end is coupled to the handle and the distal end is movable relative to the handle and dimensioned so that it remains outside the patient's body to provide a visual indicator of the position of the surgical element as it used to implant the device.

8. A method for treating female urinary incontinence comprising the steps of:

providing first and second surgical elements, each defining in part a curved shaft, and each having a distal end and a proximal end;

providing a tape having a first end coupled to the first surgical element and a second end coupled to the second surgical element;

coupling the proximal end of the first surgical element to a handle;

providing an articulating mechanical arm connected to the handle and movable relative to the handle to at least a position in which the distal end of the arm is aligned in a predetermined manner with the distal end of the first or second surgical element when coupled thereto;

passing the first surgical element into the body on one side of the urethra and through the abdomen wall while the articulating mechanical arm remains outside of the body to provide a visual indicator as to the position of the surgical element as it is passed through the body;

uncoupling the first surgical element from the handle;

coupling the proximal end of the second surgical element to the handle; and passing the second surgical element into the body on the opposite side of the urethra than the first surgical element and through the abdomen wall to thereby create a supporting sling below the urethra while the articulating mechanical arm remains outside of the body to provide a visual indicator as to the position of the second surgical element as it is passed through the body.

* * * * *